US008235960B2

(12) United States Patent
Tatsukawa et al.

(10) Patent No.: US 8,235,960 B2
(45) Date of Patent: Aug. 7, 2012

(54) ABSORBENT PRODUCT

(75) Inventors: Akiko Tatsukawa, Mima-gun (JP); Hirofumi Miyake, Mima-gun (JP)

(73) Assignee: Livedo Corporation, Ehime (JP)

( * ) Notice: Subject to any disclaimer, the term of this patent is extended or adjusted under 35 U.S.C. 154(b) by 368 days.

(21) Appl. No.: 12/464,249

(22) Filed: May 12, 2009

(65) Prior Publication Data

US 2009/0287177 A1 Nov. 19, 2009

(30) Foreign Application Priority Data

May 19, 2008 (JP) ................ P2008-130632

(51) Int. Cl.
*A61F 13/15* (2006.01)
*A61F 13/20* (2006.01)

(52) U.S. Cl. ........ 604/385.27; 604/385.101; 604/385.01

(58) Field of Classification Search ............. 604/385.01, 604/385.03, 385.101, 385.24–385.3
See application file for complete search history.

(56) References Cited

U.S. PATENT DOCUMENTS

| | | | |
|---|---|---|---|
| 6,248,098 B1 | 6/2001 | Sayama | |
| 6,699,228 B1 | 3/2004 | Chmielewski et al. | |
| 2002/0120248 A1 | 8/2002 | Onishi et al. | |
| 2003/0114819 A1 | 6/2003 | Sayama et al. | |
| 2003/0216705 A1 | 11/2003 | Coates | |
| 2006/0173435 A1 | 8/2006 | Nakajima et al. | |
| 2009/0018519 A1 | 1/2009 | Yoshida | |

FOREIGN PATENT DOCUMENTS

| | | |
|---|---|---|
| CN | 1937987 | 3/2007 |
| EP | 1 731 124 | 12/2006 |
| JP | 3406205 | 5/2003 |
| JP | 2007-300940 | 11/2007 |

OTHER PUBLICATIONS

European Search Report issued Jul. 22, 2009 in corresponding to European Patent Application No. 09 00 6347.

*Primary Examiner* — Michele M Kidwell
(74) *Attorney, Agent, or Firm* — Wenderoth, Lind & Ponack, L.L.S.

(57) ABSTRACT

In an absorbent product in which an absorbent sheet member having an opening and a back sheet are overlapped, a rear pocket is formed between a rear absorbent core of the absorbent sheet member and the back sheet, and side pockets are formed on both sides of the opening. By contracting elastic members bonded to a core covering sheet on the both sides of the opening, the core covering sheet of the absorbent sheet member and the back sheet largely stand up in each side pocket, and the rear absorbent core is raised upward. Thus, it is possible to keep the distance large in a thickness direction between the absorbent sheet member and the back sheet in the vicinity of the opening and to fit a portion around the opening of the absorbent sheet member to a wearer.

18 Claims, 4 Drawing Sheets

ABSORBENT PRODUCT

BACKGROUND OF THE INVENTION

1. Field of the Invention

The present invention relates to an absorbent product for receiving excrement from a wearer.

2. Description of the Background Art

Conventionally, in a case where loose stool containing much moisture is excreted in an absorbent product such as a disposal diaper, various suggestions have been made for preventing the loose stool from expanding between a wearer and the absorbent product and adhering to the wearer over a wide range.

Japanese Patent Application Laid-Open No. 2007-300940 (Document 1) discloses a disposable wearing article including a sheet liner having an opening which is formed at its center portion and faces a wearer's anus. The liner is provided on a semi-rigid absorbent panel fixed on a back sheet, so as to face a rear waist region of the absorbent panel, and loose stool which has passed through the opening formed in the liner is kept in a small space between the liner and the absorbent panel, to thereby prevent adhesion of the loose stool to the wearer. In Document 1, an elastic member is bonded to the liner along the peripheral edge of the opening formed in the liner to maintain a form of the opening, and elastic members extending in a longitudinal direction on the both sides in a width direction of the opening are bonded to the liner so that the liner is lifted up apart from the absorbent panel.

Japanese Patent Gazette No. 3406205 (Document 2) discloses a disposable diaper where a sheet-like top wall is provided between distal edges (i.e., both upper portions) of a pair of side walls which extend in a longitudinal direction on the both sides in a width direction and stand toward a wearer. A cavity is formed by an absorbent core, the pair of side walls, and the top wall which faces the absorbent core with a space, and the excrement which has passed through an opening formed in the top wall is kept in the cavity. In the disposable diaper of Document 2, a pad member which is preferably formed of crimped synthetic fibers or a soft foam plastic sheet such a as urethane foam sheet is provided around the opening formed in the top wall to prevent the opening in the top wall from shifting in the wearer's anus or the like.

In the disposable wearing article of Document 1, since the liner is a thin sheet in which two sheets are laminated and the liner contacts the absorbent panel by the body pressure of wearer or the like, there is a possibility that the space formed between the liner and the absorbent panel is lost and the loose stool or the like cannot be kept in the space. Further, the liner is twisted by the movement of wearer and the opening may be shifted from the wearer's anus or the like.

Similarly in the disposable diaper of Document 2, since the top wall (excluding a portion around the opening) is a thin sheet and the top wall contacts the absorbent core by the body pressure of wearer or the like, there is a possibility that the cavity is lost and the loose stool or the like cannot be kept in the cavity. Further, in the disposable diaper of Document 2, the side walls and the outer surface of the top wall have hydrophobicity (preferably, hydrophobicity and liquid imperviousness). If the opening is shifted from the anus or the like even if only slightly, the excrement which has not passed through the opening expands onto the front and back of the disposable diaper along the top wall and adheres to the wearer widely.

BRIEF SUMMARY OF THE INVENTION

The present invention is intended for an absorbent product for receiving excrement from a wearer. It is an object of the present invention to keep the distance large in a thickness direction between an absorbent sheet member and a back sheet in the vicinity of an opening in the absorbent product and to fit a portion around the opening of the absorbent sheet member to the wearer.

The absorbent product comprises: a back sheet; and an absorbent sheet member which is overlapped on the back sheet and bonded to the back sheet, the absorbent sheet member having an opening to come into contact with a crotch region of a wearer, and in the absorbent product, the absorbent sheet member comprises: a front absorbent core to be positioned on a front side of the wearer; a rear absorbent core to be positioned on a back side of the wearer; a liquid-pervious core covering sheet for covering the front absorbent core and the rear absorbent core, the opening being formed between the front absorbent core and the rear absorbent core; and a pair of elastic members extending in a longitudinal direction which is an arrangement direction of the front absorbent core and the rear absorbent core, being bonded to the core covering sheet on both side portions in a width direction perpendicular to the longitudinal direction, the pair of elastic members is at least provided from outsides in the width direction of the opening to positions where the pair of elastic members overlaps with the rear absorbent core, contracting to draw the rear absorbent core toward the front absorbent core, both end portions outside the pair of elastic members in the width direction of the core covering sheet are bonded to the back sheet on both sides in the width direction of the opening, to form side pockets between the core covering sheet and the back sheet, and an outer portion of the rear absorbent core of the absorbent sheet member, excluding a portion around the opening, is bonded to the back sheet, to form a rear pocket between the rear absorbent core and the back sheet. With this structure, it is possible to keep the distance large in the thickness direction between the absorbent sheet member and the back sheet in the vicinity of the opening and to fit a portion around the opening of the absorbent sheet member to the wearer.

According to a preferred embodiment of the present invention, a width of the rear absorbent core in the vicinity of the opening is gradually decreased as being closer to the front absorbent core. It is thereby possible to increase the distance in the thickness direction between the absorbent sheet member and the back sheet in the side pockets and to fit a portion around the opening of the absorbent sheet member to the wearer. More preferably, the pair of elastic members is located at outsides in the width direction of the rear absorbent core in the vicinity of the opening.

According to another preferred embodiment of the present invention, the front absorbent core and the rear absorbent core are apart from each other with respect to the longitudinal direction.

According to still another preferred embodiment of the present invention, portions of the pair of elastic members overlapping with the rear absorbent core are located on a side of the rear absorbent core toward the back sheet. According to still another preferred embodiment of the present invention, the pair of elastic members extends in the longitudinal direction from positions on the rear absorbent core to positions on the front absorbent core, and an outer portion of the front absorbent core of the absorbent sheet member, excluding a portion around the opening, is bonded to the back sheet, to form a front pocket between the front absorbent core and the back sheet. It is thereby possible to further increase the holding capacity of excrement.

In the absorbent product, the back sheet may comprise: a water-repellent or liquid-impervious outer covering sheet; and a hydrophilic sheet laminated on the outer covering sheet.

Or, the back sheet may comprise: a water-repellent or liquid-impervious outer covering sheet; and a high absorbent resin layer provided on the outer covering sheet.

Further, the absorbent product may comprise a pair of side wall parts which is provided over almost entire length in the longitudinal direction on both sides in the width direction of the back sheet. The absorbent product may be an auxiliary absorbent pad which is attached on an exterior product of a wearer.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
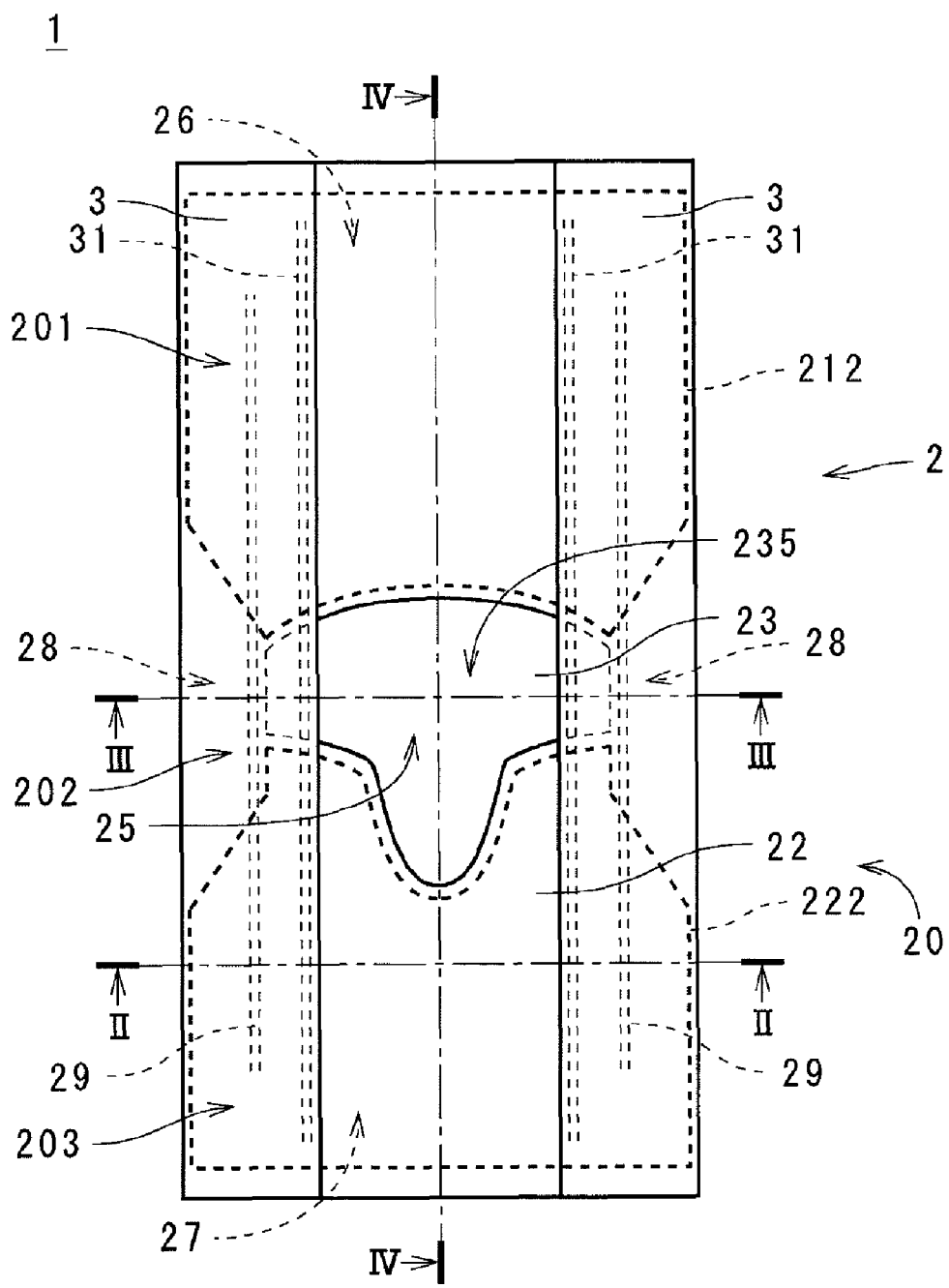
FIG. 1 is a plan view of an absorbent product in accordance with a preferred embodiment.

FIG. 1 is a plan view showing an expanded absorbent product 1 in accordance with a preferred embodiment of the present invention. The absorbent product 1 is an auxiliary absorbent pad which is attached on the inner side of a disposal diaper and the like to receive excrement such as loose stool from the wearer. FIG. 1 shows a side of the absorbent product 1 which is in contact with a wearer.

As shown in FIG. 1, the absorbent product 1 has a sheet-like main body part 2 which is substantially rectangular in plan view and a pair of side wall parts 3 which are provided over almost the entire length in a longitudinal direction perpendicular to a width direction, on both sides in the width direction of the main body part 2 (i.e., the both sides are both sides in the horizontal direction of FIG. 1 and are those in the width direction of an absorbent sheet member 20 discussed later). In the absorbent product 1, the side wall parts 3 stand up toward the upper side (i.e., the side toward the wearer) on the both sides of the main body part 2 by contracting elastic members 31 provided in the side wall parts 3, to form standing gathers which come into contact with the vicinity of wearer's crotch in wearing.

As the side wall parts 3, water-repellent or liquid-impervious nonwoven fabric (i.e., spunbond nonwoven fabric, melt-blown nonwoven fabric, or SMS nonwoven fabric) made of hydrophobic fiber (e.g., polypropylene, polyethylene, polyester, polyamide, or nylon) are used. As the elastic members 31, polyurethane yarn, strip-like polyurethane film, yarn-like or strip-like natural rubber, or the like are used for example.

An upper portion 201 and a lower portion 203 of the main body part 2 in FIG. 1 are a portion to be positioned on the front side of the wearer and a portion to be positioned on the back side, respectively, and they are referred to as a "front part 201" and a "rear part 203" in the following description. A portion 202 which is continuously formed from the front part 201 and the rear part 203 between the front part 201 and the rear part 203 and is to come into contact with a crotch region of the wearer, is referred to as a "middle part 202".

Figure 2:
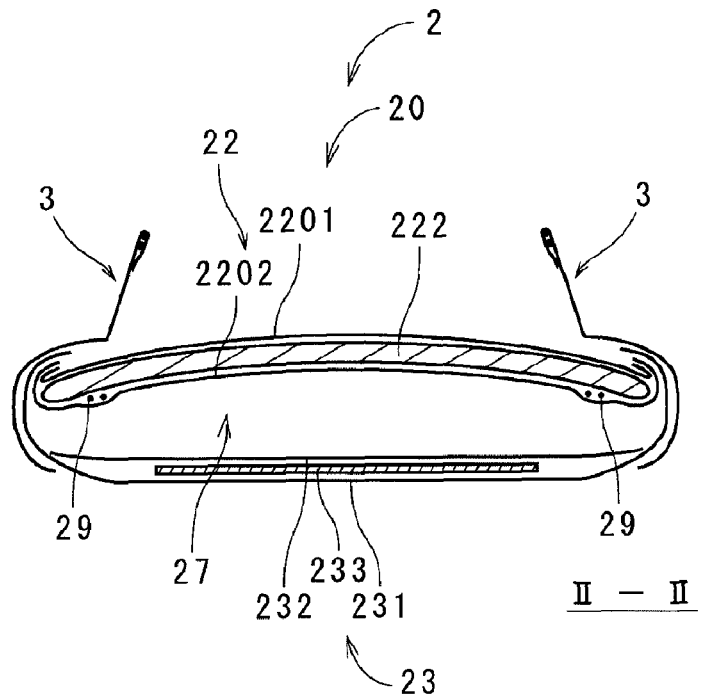
FIGS. 2 to 4 are cross-sectional views of the absorbent product.
Figure 3:
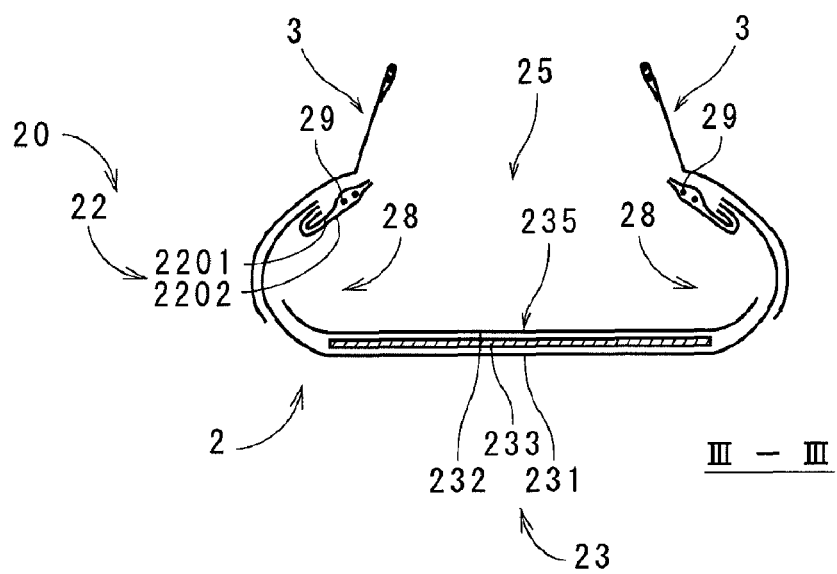
Figure 4:
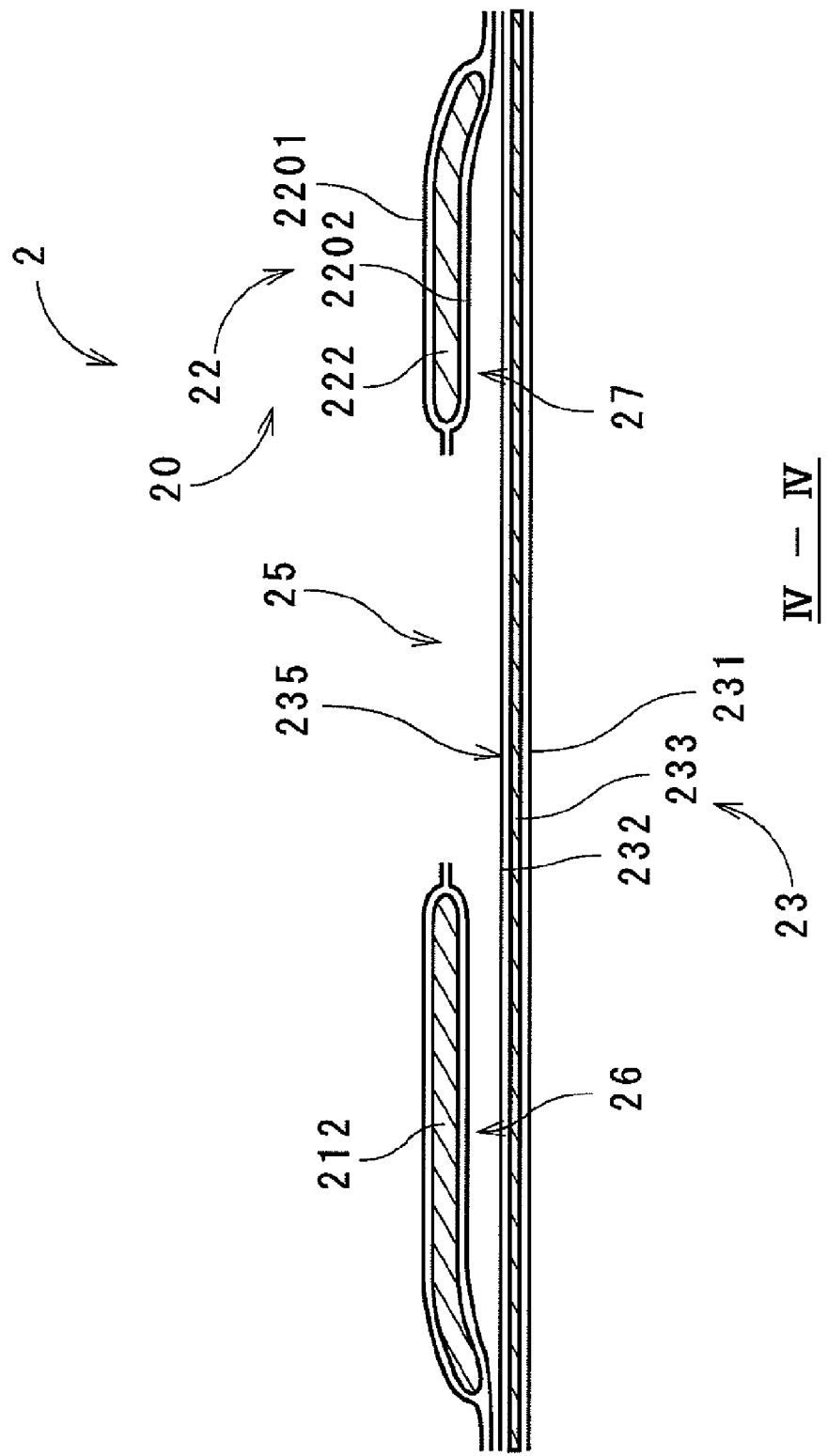

FIG. 2 is a cross-sectional view of the absorbent product 1 by a plane perpendicular to the longitudinal direction (i.e., the vertical direction of FIG. 1) of the absorbent product 1 at the positions indicated by arrows II-II of the rear part 203 shown in FIG. 1, and FIG. 3 is a cross-sectional view of the absorbent product 1 by a plane perpendicular to the longitudinal direction at the positions indicated by arrows of the middle part 202. FIG. 4 is a cross-sectional view of the absorbent product 1 by a plane perpendicular to the width direction of the absorbent product 1 at the positions indicated by arrows IV-IV shown in FIG. 1. The constitution of the front part 201 is almost the same as that of the rear part 203, and a cross-sectional view of the front part 201 by a plane perpendicular to the longitudinal direction is the same as FIG. 2 in the absorbent product 1.

As shown in FIGS. 1 to 4, the main body part 2 has a back sheet 23 and the absorbent sheet member 20 which is overlapped on the back sheet 23 (i.e., overlapped on a side of the back sheet 23 toward the wearer) and is bonded to the back sheet 23 in the peripheral edges. An opening 25 to come into contact with the crotch region of the wearer is formed in the almost central portion in the longitudinal direction of the absorbent sheet member 20, and the width of the opening 25 is made smaller than that of the absorbent product 1, as shown in FIGS. 1, 3 and 4. The back sheet 23 has a central exposed area 235 which is exposed in the opening 25 of the absorbent sheet member 20 and is directly to come into contact with the crotch region of the wearer.

As shown in FIGS. 1 and 4, the absorbent sheet member 20 has a front absorbent core 212 to be positioned on the front side (stomach side) of the wearer in wearing the absorbent product 1, a rear absorbent core 222 which is apart from the front absorbent core 212 in the longitudinal direction and is to be positioned on the back side of the wearer, and a liquid-pervious core covering sheet 22 for covering upper surfaces and lower surfaces of the front absorbent core 212 and the rear absorbent core 222 (i.e., surfaces of the front absorbent core 212 and the rear absorbent core 222 toward the wearer and surfaces of the front absorbent core 212 and the rear absorbent core 222 toward the back sheet 23). In FIG. 1, the outer forms of the front absorbent core 212 and the rear absorbent core 222 are drawn by thick broken lines.

As shown in FIG. 1, an edge of the rear absorbent core 222 toward (i.e., along) the opening 25 and an edge of the opening 25 toward (i.e., along) the rear absorbent core 222 are concave with respect to the longitudinal direction, and an edge of the front absorbent core 212 toward the opening 25 and an edge of the opening 25 toward the front absorbent core 212 are also concave with respect to the longitudinal direction. The edge of the rear absorbent core 222 toward the opening 25 and the edge of the opening 25 toward the rear absorbent core 222 are largely concave in the centers in the width direction in comparison with their both side portions, and the both edges are largely apart from the front absorbent core 212. In other words, a radius of curvature in the centers in the width direction is smaller than those in the other portions in the edge of the rear absorbent core 222 toward the opening 25 and the edge of the opening 25 toward the rear absorbent core 222.

As shown in FIGS. 2 and 4, the core covering sheet 22 has a first covering sheet 2201 for covering upper surfaces of the front absorbent core 212 and the rear absorbent core 222 and a second covering sheet 2202 for covering lower surfaces of the front absorbent core 212 and the rear absorbent core 222. The above-described opening 25 is formed between the front absorbent core 212 and the rear absorbent core 222 in the core covering sheet 22, and a portion for covering the front absorbent core 212 of the core covering sheet 22 and a portion for covering the rear absorbent core 222 are continuously formed on the both sides in the width direction of the opening 25.

The absorbent sheet member 20 also has a pair of elastic members 29 extending in the longitudinal direction on the both sides in the width direction of the opening 25 (i.e., extending in an arrangement direction of the front absorbent core 212 and the rear absorbent core 222), as shown in FIGS. 1 to 3. For example, polyurethane yarn, strip-like polyurethane film, yarn-like or strip-like natural rubber, or the like are used as the elastic members 29. Each elastic member 29 has two polyurethane yarns in the present preferred embodiment. The elastic members 29 are at least provided from outsides in the width direction of the opening 25 to positions where the elastic members 29 overlap with the rear absorbent core 222, and the elastic members 29 extend in the longitudinal direction from positions on the rear absorbent core 222 to positions on the front absorbent core 212 in the preferred embodiment, as shown in FIG. 1.

As shown in FIGS. 1 and 2, portions of the elastic members 29 overlapping with the rear absorbent core 222 are located between the rear absorbent core 222 and the second covering sheet 2202 of the core covering sheet 22 below the rear absorbent core 222 (i.e., on a side of the rear absorbent core 222 toward the back sheet 23), and the extended elastic members 29 are bonded to the second covering sheet 2202 and the rear absorbent core 222. Portions of the elastic members 29 overlapping with the front absorbent core 212 are located between the front absorbent core 212 and the second covering sheet 2202 below the front absorbent core 212, and the extended elastic members 29 are bonded to the second covering sheet 2202 and the front absorbent core 212, similarly to the portions of the elastic members 29 overlapping with the rear absorbent core 222.

As shown in FIG. 3, portions of the elastic members 29 between the front absorbent core 212 and the rear absorbent core 222 are located in the vicinity of the opening 25 between the first covering sheet 2201 and the second covering sheet 2202 of the core covering sheet 22, and the extended elastic members 29 are bonded to the first covering sheet 2201 and the second covering sheet 2202. By contracting the pair of elastic members 29, the rear absorbent core 222 is drawn toward the front absorbent core 212 and the front absorbent core 212 is drawn toward the rear absorbent core 222, to deform the front part 201 and the rear part 203 along the wearer in the absorbent product 1 shown in FIG. 1.

As discussed above, since the front absorbent core 212 and the rear absorbent core 222 are apart from each other with respect to the longitudinal direction, the front absorbent core 212 and the rear absorbent core 222 dot not exist in both side areas in the width direction of the opening 25 (the both side areas include outside areas in the width direction of the pair of elastic members 29).

In the vicinity of both end portions in the longitudinal direction of the main body part 2, the width of the rear absorbent core 222 is made almost equal to that of the main body part 2, and the width of the front absorbent core 212 is made almost equal to that of the main body part 2, as shown in FIG. 1. In portions around the opening 25 of the rear absorbent core 222, the width of the rear absorbent core 222 is gradually decreased as being closer to the opening 25 and the front absorbent core 212 in the absorbent sheet member 20. In portions around the opening 25 of the front absorbent core 212, the width of the front absorbent core 212 is gradually decreased as being closer to the opening 25 and the rear absorbent core 222. The pair of elastic members 29 is located at outsides of the front absorbent core 212 and the rear absorbent core 222 in the vicinity of the opening 25.

The front absorbent core 212 and the rear absorbent core 222 are formed by wrapping a mixture of hydrophilic fibers (e.g., crushed pulp fibers or cellulose fibers) and granulated absorbent polymers (e.g., SAP (Super Absorbent Polymer)) in a tissue paper, a liquid-pervious nonwoven fabric or the like, and the front absorbent core 212 and the rear absorbent core 222 rapidly absorb and retain the moisture which has passed through the core covering sheet 22. The tissue paper, the liquid-pervious nonwoven fabric or the like is bonded to the hydrophilic fibers and the absorbent polymers with hot melt adhesive, to prevent deformation of the hydrophilic fibers and falling of the absorbent polymers (especially, falling after absorption of moisture).

The first covering sheet 2201 and the second covering sheet 2202 of the core covering sheet 22 is a nonwoven fabric made of liquid-pervious sheet material, for example, hydrophilic fiber, and the first covering sheet 2201 and the second covering sheet 2202 immediately catch moisture of excrement from the wearer and moves the moisture into the front absorbent core 212 and the rear absorbent core 222. Examples of nonwoven fabric used for the core covering sheet 22 are a point-bond nonwoven fabric, air-through nonwoven fabric, or spunlace nonwoven fabric, and as hydrophilic fibers for making these nonwoven fabrics, normally, cellulose, rayon, cotton or the like are used. As the core covering sheet 22, a liquid-pervious nonwoven fabric made of hydrophobic fiber (for example, polypropylene, polyethylene, polyester, polyamide, or nylon) with hydrophilic treatment using a surfactant may be utilized.

As shown in FIGS. 2 and 3, the back sheet 23 is folded toward the wearer on the both sides in the width direction of the main body part 2, and bonded to both end portions outside the pair of elastic members 29 in the width direction of the core covering sheet 22 on the core covering sheet 22 by using the hot melt adhesive or the like so that the back sheet 23 covers both end portions in the width direction of the front absorbent core 212 and the rear absorbent core 222. The pair of side wall parts 3 is bonded to both end portions in the width direction of the back sheet 23 by the hot melt adhesive or the like. As shown in FIG. 3, a surface of the core covering sheet 22 which faces the back sheet 23 directly (i.e., the surface of the core covering sheet 22 which faces the back sheet 23 in a state where there is no intervening object between the surface and the back sheet 23), is not bonded to the back sheet 23 on the both sides in the width direction of the opening 25 and at outsides in the width direction of the pair of elastic members 29 in the absorbent product 1. With this structure, a pair of side pockets 28 is formed between the core covering sheet 22 and the back sheet 23 on the both sides in the width direction of the opening 25.

The back sheet 23 has a water-repellent or liquid-impervious outer covering sheet 231, a very thin absorbent sheet 233 provided on the outer covering sheet 231 (i.e., provided on a side of the outer covering sheet 231 toward the wearer), and a hydrophilic sheet 232 which is laminated on the outer covering sheet 231 and the absorbent sheet 233 (i.e., laminated on a side of the outer covering sheet 231 and the absorbent sheet 233 toward the wearer). In other words, the absorbent sheet 233 is provided on a surface of the outer covering sheet 231, the surface being opposed to the absorbent sheet member 20, and the hydrophilic sheet 232 is laminated on the surface of the outer covering sheet 231.

As the outer covering sheet 231, water-repellent or liquid-impervious nonwoven fabric (i.e., spunbond nonwoven fabric, meltblown nonwoven fabric, or SMS nonwoven fabric) made of hydrophobic fiber (e.g., polypropylene, polyethylene, polyester, polyamide, or nylon), a water-repellent or liquid-impervious plastic film, or a laminated sheet of the water-repellent or liquid-impervious nonwoven fabric and the plastic film are used. The outer covering sheet 231 prevents moisture of excrement or the like from leaking out to the outside of the main body part 2. In a case where a plastic film is used for the outer covering sheet 231, it is preferable that a plastic film with permeability (breathability) is used as the outer covering sheet 231, from the view point of preventing sweatiness in the absorbent product 1 and providing comfortable feeling to the wearer.

The absorbent sheet 233 has two sheets and a high absorbent resin layer provided between the two sheets. The high absorbent resin layer is formed by fixing granulated absorbent polymers such as the SAP on the two sheets by using the hot melt adhesive. Examples of the two sheets are a nonwoven fabric made of hydrophilic fibers, a nonwoven fabric made of hydrophobic fiber with hydrophilic treatment, a tissue paper, or the like. The high absorbent resin layer (i.e., the granulated absorbent polymers) is located between the above two sheets in strip form extending in the longitudinal direction. In other words, an area in which the absorbent polymers do not exist is provided between two linearly layer elements of the high absorbent resin layer, the layer elements extending in the longitudinal direction. The two sheets are bonded in the areas in which the absorbent polymers do not exist, to seal each of the layer elements. Instead of the absorbent sheet 233, there may be a case where the granulated absorbent polymers such as the SAP are applied onto the outer covering sheet 231, the absorbent polymers are bonded to the outer covering sheet 231 by the hot melt adhesive or the like, and thereby the high absorbent resin layer is directly formed on the outer covering sheet 231. Examples of the hydrophilic sheet 232 are preferably a nonwoven fabric made of hydrophilic fibers such as cellulose, rayon, or cotton (e.g., spunlace nonwoven fabric) or a hydrophilic nonwoven fabric made of hydrophobic fibers (e.g., polypropylene, polyethylene, polyester, polyamide, or nylon) with hydrophilic treatment using a surfactant.

Out of an outer portion of the rear absorbent core 222 of the absorbent sheet member 20 shown in FIG. 1, a portion around the opening 25 (i.e., a portion around the opening 25 including outside areas of the pair of elastic members 29), is not bonded to the upper surface of the back sheet 23 in the main body part 2 as shown in FIG. 4. The above portion can be explained in the preferred embodiment as a portion which includes the edge of the opening 25 and portions from the edge approximately to both ends in the width direction of the main body part 2, out of the outer portion of the rear absorbent core 222. A portion excluding the above portion which is not bonded to the back sheet 23 in the outer portion of the rear absorbent core 222 is bonded to the back sheet 23, to form a rear pocket 27 between the rear absorbent core 222 and the back sheet 23 (i.e., between a portion of the absorbent sheet member 20 corresponding to the rear absorbent core 222 and the back sheet 23).

Out of an outer portion of the front absorbent core 212 of the absorbent sheet member 20 shown in FIG. 1, a portion around the opening 25 (i.e., a portion around the opening 25 including outside areas of the pair of elastic members 29), is not bonded to the upper surface of the back sheet 23 as shown in FIG. 4. The above portion can be explained in the preferred embodiment as a portion which includes the edge of the opening 25 and portions from the edge approximately to both ends in the width direction of the main body part 2, out of the outer portion of the front absorbent core 212. A portion excluding the above portion which is not bonded to the back sheet 23 in the outer portion of the front absorbent core 212 is bonded to the back sheet 23, to form a front pocket 26 between the front absorbent core 212 and the back sheet 23 (i.e., between a portion of the absorbent sheet member 20 corresponding to the front absorbent core 212 and the back sheet 23). In the absorbent product 1 shown in FIG. 1, the front pocket 26 and the rear pocket 27 are continuously formed with the pair of side pockets 28.

In the absorbent product 1, excrement such as loose stool from the wearer reaches the back sheet 23 through the opening 25 to be received by the central exposed area 235 of the back sheet 23. The excrement received by the central exposed area 235 moves to internal spaces of the rear pocket 27, the side pockets 28 and the front pocket 26 to be kept therein.

As discussed above, the pair of extended elastic members 29 bonded to the core covering sheet 22 is provided on the both sides of the opening 25 in the absorbent product 1, the elastic members 29 are contracted in the longitudinal direction, and thereby the core covering sheet 22 of the absorbent sheet member 20 largely stands up (i.e., stands toward the wearer) together with the back sheet 23, in each of the pair of side pockets 28, as shown in FIG. 3. The rear absorbent core 222 is raised upward by contracting the elastic members 29 so that the rear absorbent core 222 moves away from the back sheet 23 (i.e., so that the distance in the thickness direction between the rear absorbent core 222 and the back sheet 23 in the rear pocket 27 is increased), as shown in FIGS. 2 and 4.

With this structure, it is possible to keep the distance large in the thickness direction between the absorbent sheet member 20 and the back sheet 23 in the vicinity of the opening 25 and to fit a portion around the opening 25 of the absorbent sheet member 20 to the wearer. As a result, it is possible to surely keep and retain the excrement in the side pockets 28 and the rear pocket 27 and to prevent expansion and wide adhesion of the excrement to the wearer. As described above, since the absorbent product 1 can prevent wide expansion of the excrement, the absorbent product 1 is especially suitable for an auxiliary absorbent pad which covers a relatively narrow range of the crotch region of wearer on the inner side of an exterior product such as a disposal diaper and can be easily exchanged.

In the absorbent product 1, since the pair of elastic members 29 is arranged in the vicinity of the opening 25 in the width direction, the core covering sheet 22 of the absorbent sheet member 20 largely stands up, together with the back sheet 23, in each of the pair of side pockets 28. With this structure, it is possible to further increase the distance in the thickness direction between the absorbent sheet member 20 and the back sheet 23 in the vicinity of the opening 25 and to fit the portion around the opening 25 of the absorbent sheet member 20 to the wearer.

The front pocket 26 is formed between the absorbent sheet member 20 and the back sheet 23 in the front part 201 of the main body part 2 to increase the holding capacity of excrement in the absorbent product 1. As a result, the excrement which has not been kept in the rear pocket 27 and the side pockets 28 during excretion can be kept in the front pocket 26 or the excrement which has moved from the rear pocket 27 in exchanging the absorbent products 1 can be kept in the front pocket 26, to further suppress adhesion of the excrement to the wearer.

By contracting the pair of elastic members 29 which is continuously provided from the rear absorbent core 222 to the front absorbent core 212, the front absorbent core 212 is raised upward so that the front absorbent core 212 moves away from the back sheet 23 (i.e., so that the distance in the thickness direction between the front absorbent core 212 and the back sheet 23 in the front pocket 26 is increased). With this structure, it is possible to further increase the distance in the thickness direction between the absorbent sheet member 20 and the back sheet 23 in the vicinity of the opening 25 and to fit the portion around the opening 25 of the absorbent sheet member 20 to the wearer.

In the portions around the opening 25 of the rear absorbent core 222, the width of the rear absorbent core 222 is gradually decreased as being closer to the opening 25 and the front absorbent core 212 in the absorbent product 1 shown in FIG. 1, as discussed above. Each side pocket 28 extends toward the rear part 203 in the longitudinal direction in outsides of the rear absorbent core 222, and the areas of the core covering sheet 22 and the back sheet 23 which stand up by contraction of the elastic members 29 are increased. As a result, the core covering sheet 22 and the back sheet 23 largely stand up the upper side, and it is possible to further increase the distance in the thickness direction between the absorbent sheet member 20 and the back sheet 23 in the vicinity of the opening 25 and to fit the portion around the opening 25 of the absorbent sheet member 20 to the wearer.

Similarly, the width of the front absorbent core 212 is gradually decreased as being closer to the opening 25 and the rear absorbent core 222 in the portions around the opening 25 of the front absorbent core 212. Each side pocket 28 extends toward the front part 201 in the longitudinal direction in outsides of the front absorbent core 212 around the opening 25, and as a result, it is possible to further increase the distance in the thickness direction between the absorbent sheet member 20 and the back sheet 23 in the vicinity of the opening 25 and to fit the portion around the opening 25 of the absorbent sheet member 20 to the wearer.

Since the pair of elastic members 29 is located in outsides in the width direction of the rear absorbent core 222 and the front absorbent core 212 in the vicinity of the opening 25, the contraction force of the elastic members 29 is fully exerted in each side pocket 28 and the core covering sheet 22 and the back sheet 23 largely stand up. As a result, it is possible to further increase the distance in the thickness direction between the absorbent sheet member 20 and the back sheet 23 in the vicinity of the opening 25 and to fit the portion around the opening 25 of the absorbent sheet member 20 to the wearer.

In the absorbent product 1, since the front absorbent core 212 and the rear absorbent core 222 are apart from each other with respect to the longitudinal direction, the front absorbent core 212 and the rear absorbent core 222 do not exist in the both side areas in the width direction of the opening 25. Therefore, the flexibility of the absorbent sheet member 20 is improved in the both side areas in the width direction of the opening 25 in comparison with the other portions, and the core covering sheet 22 and the back sheet 23 largely stand up. As a result, it is possible to further increase the distance in the thickness direction between the absorbent sheet member 20 and the back sheet 23 in the vicinity of the opening 25 and to fit the portion around the opening 25 of the absorbent sheet member 20 to the wearer.

As discusses above, since the portions of the pair of elastic members 29 overlapping with the rear absorbent core 222 are located below the rear absorbent core 222, the rear absorbent core 222 stands up so as to be largely away from the back sheet 23. As a result, it is possible to further increase the distance in the thickness direction between the absorbent sheet member 20 and the back sheet 23 in the vicinity of the opening 25 and to fit the portion around the opening 25 of the absorbent sheet member 20 to the wearer. Similarly, since the portions of the pair of elastic members 29 overlapping with the front absorbent core 212 are located below the front absorbent core 212 and the front absorbent core 212 stands up so as to be largely away from the back sheet 23, it is possible to further increase the distance in the thickness direction between the absorbent sheet member 20 and the back sheet 23 in the vicinity of the opening 25 and to fit the portion around the opening 25 of the absorbent sheet member 20 to the wearer.

The hydrophilic sheet 232 is laminated on the water-repellent or liquid-impervious outer covering sheet 231 in the back sheet 23 of the absorbent product 1. Therefore, the moisture of excrement received by the central exposed area 235 of the back sheet 23 is rapidly dispersed onto the back sheet 23 in the longitudinal direction and easily directed to the internal spaces of the rear pocket 27 and the front pocket 26. Since the absorbent sheet 233 is provided on the outer covering sheet 231, the moisture of excrement can be fixed in the back sheet 23 to further suppress adhesion of the excrement to the wearer.

In the absorbent product 1, since the pair of side wall parts 3 is formed on the both sides in the width direction of the main body part 2, the excrement which has not kept in the rear pocket 27, the side pockets 28 and the front pocket 26 is prevented from leaking out from the legs of wearer.

Though the preferred embodiment of the present invention has been discussed above, the present invention is not limited to the above-discussed preferred embodiment, but allows various variations.

The portions of the pair of elastic members 29 overlapping with the rear absorbent core 222 are not necessarily bonded to the rear absorbent core 222 directly. For example, in a case where a member in which two nonwoven fabrics are laminated is used as the second covering sheet 2202, the elastic members 29 may be arranged between the two nonwoven fabrics and bonded to the rear absorbent core 222 indirectly. Similarly, the portions of the elastic members 29 overlapping with the front absorbent core 212 may be bonded to the front absorbent core 212 indirectly.

The portions of the elastic members 29 overlapping with the rear absorbent core 222 may be arranged on the rear absorbent core 222. In a case where the rear absorbent core 222 is a laminated body of a plurality of core members, the portions may be arranged between the core members (similarly in the portions of the pair of elastic members 29 overlapping with the front absorbent core 212).

The core covering sheet 22 may be one sheet member in the absorbent sheet member 20. In this case, a portion of the one sheet member for covering the upper sides of the front absorbent core 212 and the rear absorbent core 222 corresponds to the first covering sheet 2201, and a portion of the one sheet member for covering the lower sides of the front absorbent core 212 and the rear absorbent core 222 corresponds to the second covering sheet 2202. The core covering sheet 22 has only to cover at least the upper sides of the front absorbent core 212 and the rear absorbent core 222.

In the absorbent sheet member 20, the front absorbent core 212 and the rear absorbent core 222 may be provided as to be continuous in the longitudinal direction on the both sides of the opening 25. If the front absorbent core 212 and the rear absorbent core 222 are regarded as one absorbent core, the opening 25 becomes a through hole formed in the absorbent core in the middle part 202 of the main body part 2. The pair of elastic members 29 may be overlapped with the absorbent core on the both sides in the width direction of the opening 25. Even in this case, a surface of the core covering sheet 22 which faces the back sheet 23 directly is not bonded to the back sheet 23 at outsides in the width direction of the pair of elastic members 29 and the side pockets 28 are largely formed by contraction of the elastic members 29. As a result, it is possible to keep the distance large in the thickness direction between the absorbent sheet member 20 and the back sheet 23 in the vicinity of the opening 25 and to fit a portion around the opening 25 of the absorbent sheet member 20 to the wearer.

The back sheet 23 has only to have at least the water-repellent or liquid-impervious outer covering sheet 231, and one or both of the hydrophilic sheet 232 and the absorbent sheet 233 may be omitted.

Figure 5:
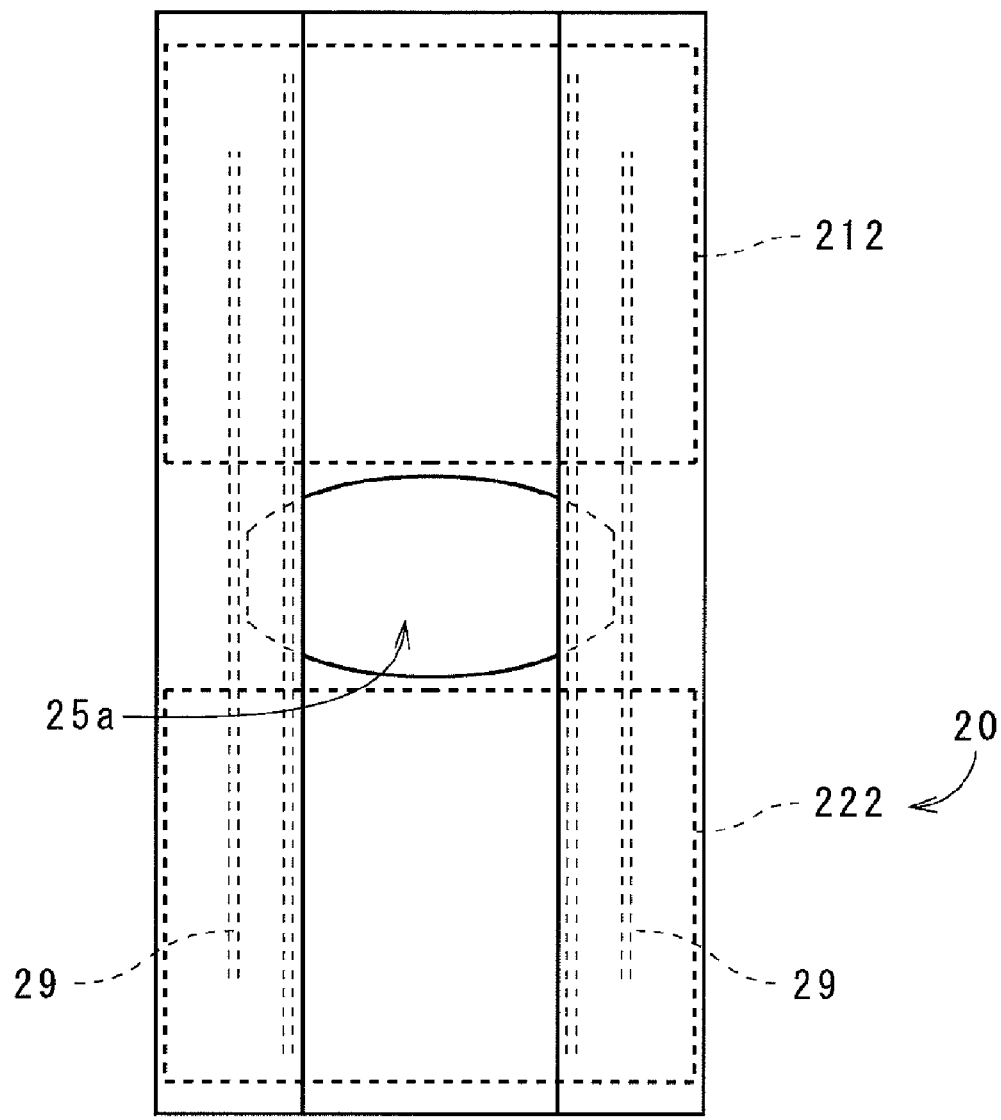
FIG. 5 is a plan view showing another example of the absorbent product.

The form of the opening 25 in plan view is not limited to that shown in FIG. 1, and the widths of the front absorbent core 212 and the rear absorbent core 222 are not necessarily gradually decreased in the vicinity of the opening 25. For example, like an absorbent product 1a shown in FIG. 5, the form of an opening 25a in plan view may be a substantially ellipse, and the widths of the front absorbent core 212 and the rear absorbent core 222 may be constant. In the absorbent product 1a, the pair of elastic members 29 overlaps with the front absorbent core 212 and the rear absorbent core 222 in the vicinity of the opening 25a, and an absorbent core do not exist in a portion in the longitudinal direction of the absorbent sheet member 20 corresponding to the opening 25a (i.e., the portion is a portion in the longitudinal direction of the absorbent sheet member 20 where the opening 25a is formed). In the absorbent product 1a, although the widths of the substantially rectangular front absorbent core 212 and rear absorbent core 222 are made equal in plan view, for example, the width of the front absorbent core 212 is made smaller than that of the rear absorbent core 222.

In the absorbent product 1 shown in FIG. 1, for example, in a case where the excrement can be surely kept in the rear pocket 27 and the side pockets 28, the front pocket 26 may not be provided. In this case, an almost entire surface of a portion of the absorbent sheet member 20 corresponding to the front absorbent core 212 is bonded to the back sheet 23.

The structure of the absorbent product 1 may be applied to, e.g., a pants-type disposal diaper having a waist opening at an upper end and a pair of leg openings on a lower part or an open-type disposal diaper where a portion located on the front side of a wearer and a portion located on the back side are fastened around waistline of the wearer in wearing the disposal diaper, as well as an auxiliary absorbent pad which is attached on (the inner side of) an exterior product.

While the invention has been shown and described in detail, the foregoing description is in all aspects illustrative and not restrictive. It is therefore understood that numerous modifications and variations can be devised without departing from the scope of the invention.

This application claims priority benefit under 35 U.S.C. Section 119 of Japanese Patent Application No. 2008-130632 filed in the Japan Patent Office on May 19, 2008, the entire disclosure of which is incorporated herein by reference.

What is claimed is:

1. An absorbent product for receiving excrement from a wearer, the absorbent product comprising:
   a back sheet; and
   an absorbent sheet member which is overlapped on said back sheet and bonded to said back sheet, said absorbent sheet member having an opening to come into contact with a crotch region of a wearer, wherein
   said absorbent sheet member comprises:
   a front absorbent core to be positioned on a front side of said wearer;
   a rear absorbent core to be positioned on a back side of said wearer;
   a liquid-pervious core covering sheet for covering said front absorbent core and said rear absorbent core, said opening being formed between said front absorbent core and said rear absorbent core, and said front absorbent core and said rear absorbent core being arranged in a longitudinal direction; and
   a pair of elastic members extending in the longitudinal direction, said elastic members being disposed on both side portions of said opening in a width direction perpendicular to the longitudinal direction,
   said elastic members are disposed at positions outside said opening in the width direction and extend to positions where said pair of elastic members overlaps with said rear absorbent core, said elastic members are bonded to said core covering sheet at said positions outside of said opening in the width direction and bonded to said rear absorbent core at said positions where said pair of elastic members overlaps with said rear absorbent core, and said elastic members contract to draw said rear absorbent core toward said front absorbent core,
   said core covering sheet has end portions disposed outside said pair of elastic members in the width direction, and the end portions are bonded to said back sheet on both sides of the opening in the width direction to form side pockets between said core covering sheet and said back sheet, and
   an outer portion of said rear absorbent core of said absorbent sheet member, excluding a portion around said opening, is bonded to said back sheet, to form a rear pocket between said rear absorbent core and said back sheet.

2. The absorbent product according to claim 1, wherein a width of said rear absorbent core in the vicinity of said opening narrows in a direction toward said front absorbent core.

3. The absorbent product according to claim 2, wherein said pair of elastic members is located at outsides in the width direction of said rear absorbent core in the vicinity of said opening.

4. The absorbent product according to claim 3, wherein said front absorbent core and said rear absorbent core are spaced apart from each other in the longitudinal direction.

5. The absorbent product according to claim 4, wherein portions of said pair of elastic members overlapping with said rear absorbent core are disposed between the back sheet and the rear absorbent core in a thickness direction of the absorbent product.

6. The absorbent product according to claim 5, wherein said pair of elastic members extends in the longitudinal direction from positions on said rear absorbent core to positions on said front absorbent core, and
   an outer portion of said front absorbent core of said absorbent sheet member, excluding a portion around said opening, is bonded to said back sheet, to form a front pocket between said front absorbent core and said back sheet.

7. The absorbent product according to claim 1, wherein said front absorbent core and said rear absorbent core are spaced apart from each other in the longitudinal direction.

8. The absorbent product according to claim 7, wherein portions of said pair of elastic members overlapping with said rear absorbent core are disposed between the back sheet and the rear absorbent core in a thickness direction of the absorbent product.

9. The absorbent product according to claim 8, wherein said pair of elastic members extends in the longitudinal direction from positions on said rear absorbent core to positions on said front absorbent core, and
   an outer portion of said front absorbent core of said absorbent sheet member, excluding a portion around said opening, is bonded to said back sheet, to form a front pocket between said front absorbent core and said back sheet.

10. The absorbent product according to claim 7, wherein said pair of elastic members extends in the longitudinal direction from positions on said rear absorbent core to positions on said front absorbent core, and
an outer portion of said front absorbent core of said absorbent sheet member, excluding a portion around said opening, is bonded to said back sheet, to form a front pocket between said front absorbent core and said back sheet.

11. The absorbent product according to claim 1, wherein portions of said pair of elastic members overlapping with said rear absorbent core are disposed between the back sheet and the rear absorbent core in a thickness direction of the absorbent product.

12. The absorbent product according to claim 11, wherein said pair of elastic members extends in the longitudinal direction from positions on said rear absorbent core to positions on said front absorbent core, and
an outer portion of said front absorbent core of said absorbent sheet member, excluding a portion around said opening, is bonded to said back sheet, to form a front pocket between said front absorbent core and said back sheet.

13. The absorbent product according to claim 1, wherein said pair of elastic members extends in the longitudinal direction from positions on said rear absorbent core to positions on said front absorbent core, and
an outer portion of said front absorbent core of said absorbent sheet member, excluding a portion around said opening, is bonded to said back sheet, to form a front pocket between said front absorbent core and said back sheet.

14. The absorbent product according to claim 1, wherein said back sheet comprises:
a water-repellent or liquid-impervious outer covering sheet; and
a hydrophilic sheet laminated on a surface of said outer covering sheet, said surface being opposed to said absorbent sheet member.

15. The absorbent product according to claim 1, wherein said back sheet comprises:
a water-repellent or liquid-impervious outer covering sheet; and
a high absorbent resin layer provided on a surface of said outer covering sheet, said surface being opposed to said absorbent sheet member.

16. The absorbent product according to claim 1, further comprising a pair of side wall parts which is provided over almost an entire length in the longitudinal direction on both sides in the width direction of said back sheet.

17. The absorbent product according to claim 1, wherein said absorbent product is an auxiliary absorbent pad which is attached on an exterior product of a wearer.

18. The absorbent product according to claim 1, wherein a contractive force of the elastic members biases the absorbent sheet member away from the back sheet in a thickness direction perpendicular to the longitudinal direction and perpendicular to the width direction.

* * * * *